US006759388B1

(12) United States Patent
Marchant et al.

(10) Patent No.: US 6,759,388 B1
(45) Date of Patent: Jul. 6, 2004

(54) SURFACTANTS THAT MIMIC THE GLYCOCALYX

(75) Inventors: Roger E. Marchant, Cleveland Heights, OH (US); Tianhong Zhang, Rockport, MA (US); Yongxing Qiu, Atlanta, GA (US); Mark A. Ruegsegger, Cleveland Heights, OH (US)

(73) Assignee: Nanomimetics, Inc., Cleveland Heights, OH (US)

( * ) Notice: Subject to any disclaimer, the term of this patent is extended or adjusted under 35 U.S.C. 154(b) by 0 days.

(21) Appl. No.: 09/302,195

(22) Filed: Apr. 29, 1999

(51) Int. Cl.[7] .............................................. B32B 27/00
(52) U.S. Cl. ................................ 514/8; 514/2; 530/300
(58) Field of Search .......................... 514/8; 525/54.3, 525/300, 312, 937

(56) References Cited

U.S. PATENT DOCUMENTS 5,741,852 A * 4/1998 Marchant .................... 525/54.3
5,897,955 A * 4/1999 Drumheller ................. 428/422

OTHER PUBLICATIONS

Qiu, "Novel oligosaccharide surfactant polymers derived from poly(vinylamine) with pendant dextran and hexanoyl groups" 1998, Macromolecules, vol. 31, pp. 165–171.*
Marchant, "Biosynthetic surfactants: novel biomimetic surface modifications for biomedical deposit resistance" 1997, American Chemical Society Conference.*

"Biomimetic engineering of non–adhesive glycocalyx–like surfaces using oligosaccharide surfactant polymers" by Holland, et al. *Nature,* vol. 392, Apr. 23, 1998, pp. 799–801.

* cited by examiner

*Primary Examiner*—Christopher Tate
*Assistant Examiner*—Roy Teller
(74) *Attorney, Agent, or Firm*—Benesch, Friedlander Coplan & Aronoff, LLP

(57) ABSTRACT

Comblike, surfactant polymers for changing the surface properties of biomaterials are provided. Such surfactant polymers comprise a polymeric backbone of repeating monomeric units having functional groups for coupling with side chains, a plurality of hydrophobic side chains linked to said backbone via the functional groups, and a plurality of hydrophilic side chains linked to said backbone via the functional groups. The hydrophobic side chains comprise an alkyl group comprising from 2 to 18 methylene groups. The alkyl groups are linked to the polymeric backbone through ester linkages, secondary amine linkages, or, preferably, amide linkages. The hydrophilic side chain is selected from the group consisting of: a neutral oligosaccharide, which, preferably, has weight average molecular weight of less than 7000; a charged oligosaccharide, preferably a negatively charged oligosaccharide having a weight average molecular weight of less than 10,000; an oligopeptide of from about 3 to about 30 amino acid residues, said oligopeptide having an amino acid sequence which interacts with protein receptors on the surface of cells; and combinations thereof. Methods of making the surfactant polymers and using the surfactant polymers to alter the surface properties of a biomaterial are also provided.

11 Claims, 5 Drawing Sheets

Phase contrast images of HUVECs on surfactant coated surfaces after 72 hours. The cells grew only on the peptide surfactants, not the saccharide surfactants. Fibronectin is a positive control surface.

SURFACTANTS THAT MIMIC THE GLYCOCALYX

This invention was made in part with government support under Grant Number RO1-HL-40047 from the National Institutes of Health. The government has certain rights in this invention.

BACKGROUND OF THE INVENTION

The present invention provides comblike surfactant polymers that are useful for changing the surface properties of synthetic biomaterials, particularly implantable biomaterials.

The use of synthetic biomaterials to sustain, augment, or completely replace diseased human organs has increased tremendously over the past thirty years. Synthetic biomaterials are used in synthetic implants such as vascular grafts, heart valves, and ventricular assist devices that have cardiovascular applications. Synthetic biomaterials are also used in extracorporeal systems and a wide range of invasive treatment and diagnostic systems. Unfortunately, existing biomaterials suffer from well-known problems associated with surface-induced thrombosis or clot formation, such as thrombotic occlusion and thromboemboli, and infection.

There have been several attempts to create nonthrombogenic surfaces on synthetic implants thereby increasing the blood-biocompatibility of implants. Early attempts included precoating the implants with proteins not involved in thrombosis, such as albumin, to mask the thrombogenic surface of the implant. However, such implants lose their nonthrombogenic properties within a short time. Attempts have been made to mask the thrombogenic surface by coating gelatin onto implants such as ventricular assist devices. While the gelatin coating reduced the thrombus formation, it did not adhere to the implant and it did not prevent thromboemboli and infection.

Attempts have been made to render implants nonthrombogenic by coating the surface of the implant with polyethylene oxide to mask the thrombogenic surface of the implant. At times this treatment reduced protein adsorption and thrombogenesis However, the coupling of polyethylene oxide to the surface of the implant involves complex chemical immobilization procedures. Moreover, the coated implants do not consistently exhibit protein resistance because of the lack of control over the density of immobilized polyethylene oxide.

There have been many attempts to prepare nonthrombogenic surfaces by attaching heparin to biomaterials. However, each method requires complex immobilization procedures such that the implant surface be first modified by attachment of a coupling molecule before heparin can be attached. For example, the positively charged coupling agent tridodecylmethylammonium chloride (TDMAC) is coated onto an implant, which provides a positively charged surface and allows heparin which has a high negative charge density, to be attached. However, the heparin slowly dissociates from the surface, to expose the positively charged TDMAC surface, which is particularly thrombogenic. Thus, the TDMAC heparin coated implant is successful only for short term implants such as catheters.

Despite these considerable research efforts, synthetic biomaterials and medical devices made from such biomaterials still suffer well-known problems associated with surface-induced thrombosis and infection. Accordingly, it is desirable to have new materials that can be used to coat biomaterials and to change their surface properties. Materials that are useful for preventing undesirable adhesions, such as proteins, or promoting desirable adhesions, such as endothelial cells are especially desirable.

SUMMARY OF THE INVENTION

In accordance with the present invention, novel, comblike, surfactant polymers which are useful for changing the surface properties of biomaterials are provided. Such surfactant polymers comprise a polymeric backbone of repeating monomeric units having functional groups for coupling with side chains, a plurality of hydrophobic side chains linked to said backbone via the functional groups, and a plurality of hydrophilic side chains linked to said backbone via the functional groups. The hydrophobic side chains comprise an alkyl group ($CH_3(CH_2-)_n$) comprising from about 2 to 18 methylene groups. The alkyl groups are linked to the polymeric backbone through ester linkages, secondary amine linkages, or, preferably, amide linkages. The hydrophilic side chain is selected from the group consisting of: a neutral oligosaccharide, which, preferably, has weight average molecular weight of less than 7000; a charged oligosaccharide, preferably a negatively charged oligosaccharide having a weight average molecular weight of less than 10,000; an oligopeptide of from about 3 to about 30 amino acid residues, said oligopeptide having an amino acid sequence which interacts with protein receptors on the surface of cells; and combinations thereof. A preferred amino acid sequence which is known to interact with molecules on the surface of cells is arginine (R), glycine (G), and aspartic acid (D). The hydrophilic side chains are linked to the polymeric backbone through ester linkages, secondary amine linkages, or, preferably, amide linkages. It has been shown that effective surface modification of biomaterials can be accomplished using the surfactant polymers of the present invention without any requirements for surface coupling chemistries.

The present invention also provides an implantable, biomaterial having a comblike surfactant polymer of the present invention coated on a hydrophobic surface thereof.

DETAILED DESCRIPTION OF THE INVENTION

Figure 1:
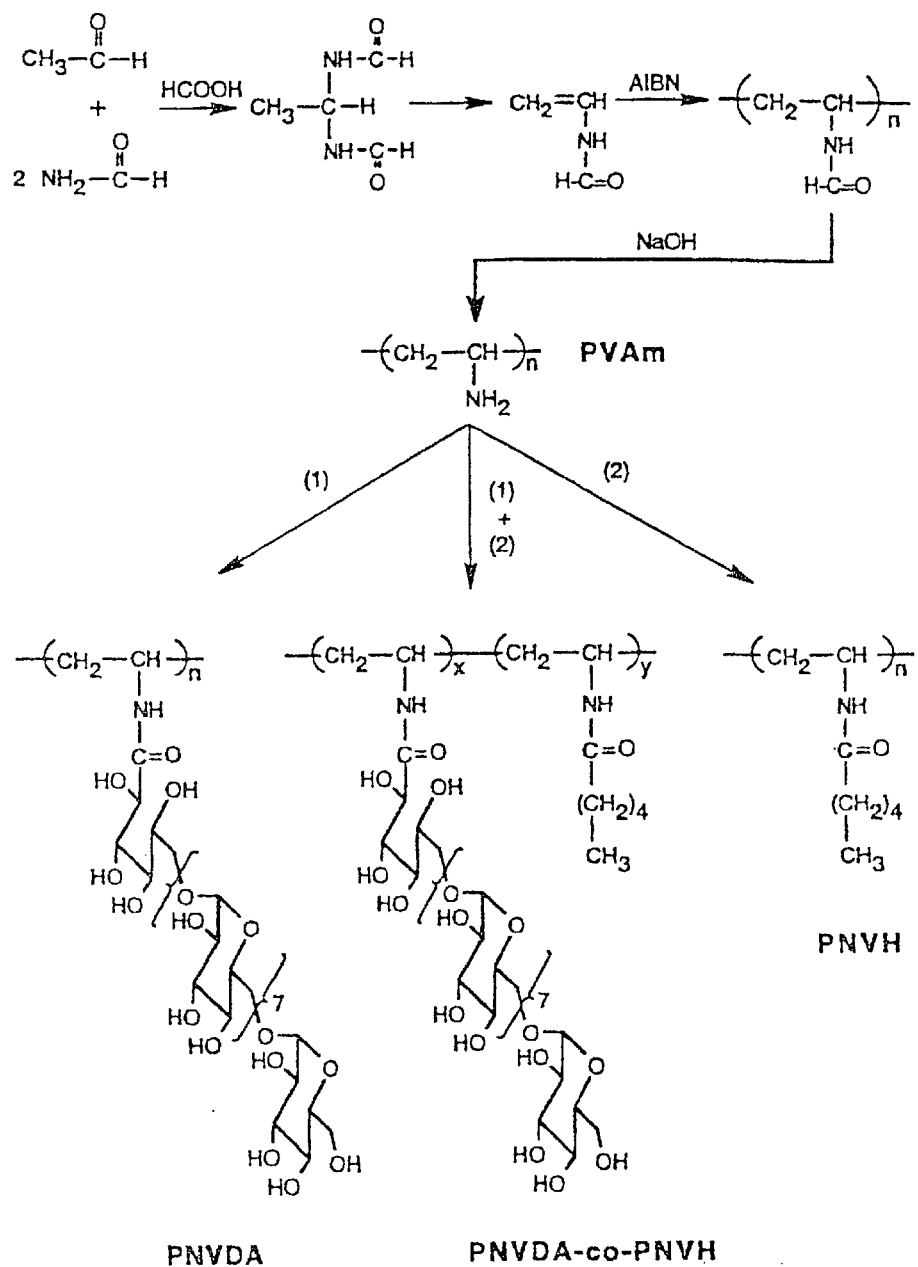
FIG. 1 is a schematic representation of the synthetic route to poly(vinyl amine) and the derivatization of poly(vinyl amine) with (1) dextran lactone and (2) (N-hexanoyloxy) succinimide.
Figure 2:
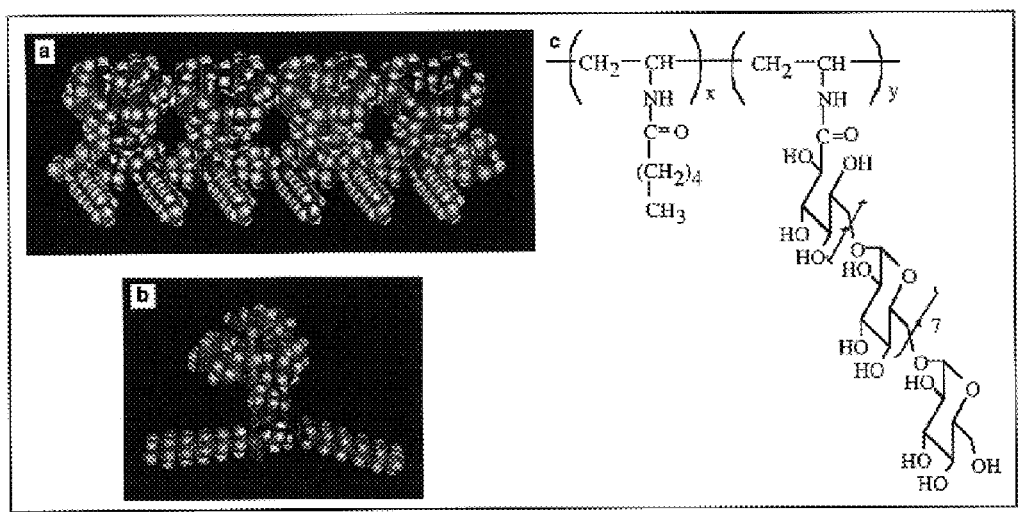
FIG. 2 shows molecular models of an oligosaccharide surfactant polymer consisting of a poly(vinyl amine) backbone with multiple dextran and alkanoyl side chains, randomly spaced. The molecular models show a portion of a 1:1.5 dextran to lauroyl surfactant polymer (surface adsorbed conformation) as an end view (a) and side view (b), with the chemical composition shown in c.

The present invention provides novel comblike surfactant polymers that mimic the glycocalyx. The glycocalyx is the oligosaccharide-rich region on the surface of cells. The glycocalyx serves to prevent undesirable biological adhesions, while proteins embedded in the cell membrane glycocalyx serve to promote desirable specific adhesions.

The comblike surfactant polymers of the present invention comprise a flexible polymeric backbone which is linked to a plurality of hydrophobic side chains and to a plurality of hydrophilic side chains. The polymeric backbone is conformationally flexible. Preferably, the polymeric backbone is formed from a homopolymer that contains a plurality of functional side groups such as for example OH groups, COOH groups, or $NH_2$ groups. Although less preferred, the polymeric backbone may be formed from a copolymer which has a combination of functional side groups. For example, the copolymer may have OH side groups and $NH_2$ side groups. Suitable homopolymers for forming the comblike surfactant polymer are, by way of example, polylysine, poly(vinyl alcohol) or poly(vinyl amine). Preferably, the polymeric backbone is formed from a poly(vinyl amine).

The hydrophopobic side chains comprise from about 2 to 18 methylene groups, preferably from about 4 to about 12 methylene groups, more preferably from about 4 to about 10 methylene groups, and are linked to the polymeric backbone via an ester linkage, a secondary amine linkage, or, preferably, an amide linkage. Preferably, the hydrophobic side chains are attached to the polymeric backbone by reacting an alkanoyl ($CH_3$—($CH_2$—)$_n$CO—)or an alkanal ($CH_3$($CH_2$—)$_n$CHO)with the homopolymer of the backbone using conventional procedures. For example, a plurality of hydrophobic side chains may be linked to poly(vinyl amine) by standard to procedures that use the corresponding N-alkanoyloxy succinimide and poly(vinyl amine) as reactants.

The hydrophilic side chain is selected from the group consisting of a neutral oligosaccharide which preferably has a weight average molecular weight of less than 7000; a charged oligosaccharide, preferably a negatively charged oligosaccharide having a weight average molecular weight of less than 10,000; an oligopeptide of from about 3 to about 30 amino acid residues said oligopeptide having an amino acid sequence which interacts with protein receptors on the surface of cells; and combinations thereof. The hydrophilic side chains are linked to the polymeric backbone through an ester linkage, a secondary amine linkage, or preferably an amide linkage. In a preferred embodiment a plurality of oligopeptides and a plurality of oligosaccharides are attached to the polymeric backbone.

To form a coating which blocks adhesion of non-specific plasma proteins on the surface of the substrate, the surfactant polymer, preferably, comprises a plurality of hydrophilic side chains formed from oligosaccharides. Such surfactant polymers may be non-ionic or ionic. Suitable oligosaccharides include, but are not limited to, neutral oligosaccharides having a weight average molecular weight of less than about 7000. Examples of such neutral oligosaccharides include dextran, which is composed of $\alpha(1\rightarrow4)$ linked glucose residues, and an oligomaltose, which is composed of $\alpha(1\rightarrow4)$ linked glucose residues. Such oligosaccharide side chains are attached to the reactive amines of the poly(vinyl amine) by standard procedures that employ the polymer and the corresponding lactone form of the oligosaccharide as reactants.

The hydrophilic side chains may also be formed from charged oligosaccharides such as, for example, the oligosaceharides that are obtained from heparin. The heparin oligosaccharides are hydrated and negatively charged which provides an additional electrostatic repulsive force that further repels plasma proteins and cellular elements such as platelets. The heparin oligosaccharide contains the unique pentasaccharide sequence that is essential for heparin's anticoagulant activity. The heparin product of deaminative cleavage of heparin possesses a terminal 2,5 anhydromanose unit. In a preferred embodiment, the terminal aldehyde of the 2,5 anhydromannose is reacted with the amines on the polymeric backbone via reductive amination to form a secondary amine.

Other suitable charged oligosaccharides for forming coatings which are non-adhesive for plasma proteins include dermatan sulfate, and dextran sulfate, which are hydrated and negatively charged and serve to repulse proteins and platelets. Preferably, these charged oligosaccharides are linked to the backbone by an amide linkage which is formed by converting the reducing end of the oligosaccharide to a lactone and then selectively reacting the lactone with the functional amine groups on the homopolymer. Alternatively, the charged oligosaccharides are linked to the backbone by reductive amination, which involves a reaction between an amine group on the polymer and a terminal aldehyde on the oligosaccharide. The resulting linkage is a secondary amine.

The ratio of hydrophobic side chains to hydrophilic oligosaccharide chains on the polymer backbone is designed to achieve a hydrophilic to hydrophobic balance that allows the surfactant to adsorb onto the hydrophobic surface of the biomaterial and, preferably, that allows the hydrophilic side chains to extend from the surface of the biomaterial into a surrounding aqueous medium. The hydrophilic to hydrophobic balance depends on the density of the hydrophobic and hydrophilic side chains and the length of the hydrophobic side chains and hydrophilic side chains. Adhesion of the adsorbing polymer onto the hydrophobic surface of the biomaterial is enhanced by increasing the length, i.e., the number of methylene groups of the hydrophobic side chain, by increasing the density of the hydrophobic side chains relative to the hydrophilic side chains, and/or by reducing the length of the hydrophilic side chains. Thus, for a surfactant polymer in which the hydrophilic side chains are formed from dextran side chains composed of 9 glucose residues and from hydrophobic alkanoyl side chains comprising 4 methylene groups, the preferred ratio of hydrophilic side chains to a hydrophobic side chains is from about 2:1 to about 1:6, more preferably from about 1:1 to about 1:5 If the hydrophobic side chains comprise 10 methylene groups and the hydrophilic side chains are dextran side chains composed of 9 glucose residues, the preferred ratio of hydrophilic side chains to hydrophobic side chains from 3:1 to about 1:5, more preferably from about 2:1 to about 1.3.

In those cases where the ratio of oligosaccharide side chains to hydrophobic side chains on the resulting surfactant polymer is low, i.e., about 1:1, there may be some unreacted functional groups, such as for example residual amine groups, which are available to bind to plasma proteins. Preferably, such unreacted functional groups are blocked or capped by further reacting the resulting surfactant polymer with organic molecules that are small relative to the hydrophilic side chains prior to application of the surfactant to the biomaterial. Suitable small organic molecules are, by way of example, glucose, maltose, and acetaldehyde.

Surfactant polymers useful for changing the surface properties of a biomaterial may also be comprised of a polymeric backbone, a plurality of hydrophobic side chains, and a plurality of hydrophilic side chains formed from polyethylene oxide. Mono-aldehyde terminated polyethylene oxide side chains are linked to the polymeric backbone via reductive amination to form a secondary amine.

In another embodiment, the suactant polymer comprises a plurality of hydrophilic oligopeptide sides chains capable of interacting with specific protein receptors on the surface of animal cells such as, for example, endothelial cells. The oligopeptide side chains act as ligands for binding the cells to the surface of the biomaterial. The oligopeptide side chains comprise from about 3 to about 30 amino acid residues. Preferably, the oligopeptide comprises the amino acid sequence RGD, more preferably RGDS, most preferably RGDSP. Alternatively, the oligopeptide comprises one of the following amino acid sequences: (i) RRAR, (ii) RRRKRR, (iii) PPRRARVT, or (iv) PPREVVPRPRP. In a preferred embodiment the oligopeptide comprises the sequence GSSSGRGDSPX, wherein X is alanine or another hydrophobic amino acid residue. The oligopeptide ligands are linked to the homopolymer backbone by an ester linkage, a secondary amine linkage, or an amide linkage.

Comblike surfactant polymers that comprise hydrophobic side chains, oligopeptide side chains, and oligosaccharide side chains are useful for providing a glycocalyx-like coating on the surface of a biomaterial. Such glycocalyx-like coatings prevent adhesion of plasma proteins to the coated surface of the biomaterial as compared to an uncoated hydrophobic surface of the biomaterial. Such coatings promote adhesion of selected cells, particularly endothelial cells, to the coated surface of the biomaterial.

The surfactants are used to coat one or more surfaces of a hydrophobic biomaterial, including a flexible, hydrophobic material. Such biomaterials are used to make implantable medical devices such as for example heart valves, stents, vascular grafts and catheters. Preferably, the surfactant is used to coat a surface which will come into contact with the blood or other body fluid of the patient following implantation of the device in the patient. The substrate is any material demonstrating biocompatibility and sufficient hydrophobicity to bind the surfactant, such as, for example, graphite and polyethylene. Other suitable biomaterials include, for example: polystyrene, polyesters, for example: Dacron®, carbon in pyrolytic carbon; polycarbonate; polymer membranes, for example, cellulose acetate, polyacrylonitrile; fluorocarbon polymers, for example Teflon®, Impra® and Gortex®; polysulfones; polyvinyl chloride; silicone rubber for example, Silastic®; silicone polymers; polypropylene; and polyurethanes. Suitable biomaterials also include nonpolymeric materials, such as for example, titanium, stainless steel, silicon, glass; and mixtures or composites thereof, that have been treated in a manner which renders their surfaces hydrophobic. The selection of the biomaterial depends upon the mechanical and functional properties required for forming an implantable biomedical device The comblike surfactant polymers of the present invention, preferably, are soluble in water and are easily applied to the surface of the biomaterial. Application is achieved by immersing the biomaterial in a solution, preferably an aqueous solution, comprising the surfactant polymer. The surfactant spontaneously attaches to the hydrophobic surface of the polymeric biomaterial to provide a monolayer which alters the surface properties of the hydrophobic surface. The monolayer is bonded to the biomaterial via hydrophobic interactions and is able to withstand a shear stress of 75 dynes/cm$^2$ as determined using a rotating disc system followed by infrared spectroscopic surface analysis. Following adsorption of the surfactant to the hydrophobic surface, the surfactant may be air dried and stored in the dry state.

The following examples are for purposes of illustration only and are not intended to limit the scope of the claims which are appended hereto.

Group A

Surfactants comprising a poly(vinyl) backbone linked by amide linkages to a plurality of neutral oligosaccharide side chains and a plurality of hydrophobic side chains were prepared as follows:

EXAMPLE 1

Poly(N-vinyl dextran aldonamide-co-N-vinyl hexanoamide) (PNVDA-co-PNVH) (1:1.06)

A. Materials and Methods

Acetaldehyde, formamide, formic acid, hexanoic acid, N-hydroxy succinimide and dicyclohexylcarbodiimide (DCCI) were purchased from Aldrich Chemical Co. and used as received. Dimethyl formamide (DMF) and dimethyl sulfoxide (DMSO) were purchased from Aldrich Chemical Co. and freshly distilled before use. before use. Strong anionic exchange resin Amberlite IR-400 (Sigma Chemical Co.) was rinsed with distilled water.

$^1$H-NMR spectra were recorded at ambient temperature, using a 200 MHz Varian Gemini-200 or a 400 MHz Bruker MSL-400 spectrometer, in parts per million downfield from tetramethylsilane (TMS) as internal standard and DMSO-d$_6$ or D$_2$O as solvent. Transmission IR spectra in the range of 400–4000 cm$^{-1}$ were recorded using a Digilab FTR spectrometer. The materials were ground with KBr and pressed into pellets under reduced pressure. For each sample, 256 scans were collected with a resolution of 8 cm$^{-1}$. Gel permeation chromatography (GPC) was carried out using a HEMA-BIO100 GPC column equipped with a Rainin HPXL solvent delivery system and a DYNAMAX refractive index detector. The column was calibrated with dextrans with narrow molecular weight distribution. The flow rate was 1.0 mL/min. with distilled water as eluent.

B. Synthesis of the Polymer

To obtain well-defined, defect-free, poly(vinyl amine) (PVAm), poly(N-vinyl formamide) was used as the precursor. As shown in the scheme of FIG. 1, the synthesis of PVAm involved the following four steps: (i) synthesis of ethylidene bisformamide; (ii) pyrolysis of ethylidene bisformamide to N-vinyl formamide and formamide: (iii) polymerization of N-vinyl formamide to poly(N-vinyl formamide) and (iv) hydrolysis of poly(N-vinyl formamide) to PVAm, which is precipitated as a PVAm.HCl salt and then desalted by ion exchange chromatography. The synthetic route to poly(N-vinyl dextran aldonamide-co-N-vinyl hexanoanide) (PNVDA-co-PNVH) derivatives, is also shown in FIG. 1. The product of each step was confirmed by spectroscopic analysis to ensure a well-defined final product of PVAm.

In the first step, acetaldehyde was condensed with formamide under acidic conditions to generate ethylidene bisformamide, which was purified by recrystallization. In the second step, ethylidene bisformamide was pyrolyzed to N-vinyl formamide and formamide. These two compounds are both liquids at ambient temperature, with very similar boiling points, but separation is not necessary. Thus, without any further purification, the N-vinyl formamide in the mixture was polymerized in isopropanol solution using AIBN as initiator. Poly(N-vinyl formamide) is water soluble with average molecular weight ~10,000 as determined by GPC using dextrans as standards. In the last step, poly(N-vinyl formamide) was hydrolyzed to PVAm under basic conditions, and then precipitated in concentrated HCl solution as PVAm.HCl. The hydrolysis was carried out under basic, rather than acidic, conditions in order to achieve complete conversion. Under acidic conditions, positive charges build up along polymer chain during hydrolysis, which then limits further hydrolysis of the remaining formamide. Under basic conditions, no charges build up during hydrolysis, and complete conversion can be realized. No amide peaks were observed in the IR spectrum of PVAm.HCl, instead, very strong —$NH_3^+$ peaks occur, indicating complete conversion of poly(N-vinyl formamide) to PVAm.HCl. The details of the synthesis were as follows:

i.) Ethylidene Bisformamide. To a solution of 45 g (1.0 mol) formamide and 50 g of formic acid heated to 40° C. with an oil bath, acetaldehyde (8.8 g, 0.2 mol) was added drop wise. The reaction mixture was stirred at 85° C. for 4 h. Excess formamide and formic acid were evaporated by vacuum distillation with the bath temperature below 120° C. The yellow-brown residue was refluxed in acetone (300 mL) and then cooled to −70° C. to precipitate white crystals. The crystals were filtered and dried under vacuum at 70° C. to give 15.0 g (65%) of ethylidene bisformamide, which was further purified by recrystallization from a mixture of isopropanol and hexane. IR (KBr): 3211 $cm^{-1}$ (v(N—H)), 2900 $cm^{-1}$, 3042 $cm^{-1}$ (v(C—H) of $CH_3$ and CH), 1689 $cm^{-1}$ (amide I), 1545 $cm^{-1}$ (amide II). $^1$H-NMR (DMSO-$d_6$, ppm): 1.24–1.31 (3H, —$CH_3$), 5.56–5.59 (1H, $CH_3$—C<u>H</u>—), 7.92–8.15 (2H, from two —CHO), 8.40–8.64 (2H, from two —CONH—).

ii.) N-Vinyl Formamide. A mixture of 6.96 g (60 mmol) ethylidene bisformamide and 2.0 g calcium carbonate was heated to 210° C. under vacuum with a sodium nitrite bath. The pyrolyzed product was vacuum distilled to give 5.80 g (91%) of a slightly yellow liquid consisting of a 1:1 molar ratio of N-vinyl formamide and formamide. $^1$H-NMR (DMSO-$D_6$, ppm): 4.19–4.76 (2H, <u>$CH_2$</u>=CH—), 6.60–6.94 (1H, $CH_2$=C<u>H</u>—), 7.23–7.47 (2H, —$NH_2$), 7.84–8.09 (2H, HCO—), 10.02 (1H, —CONH—).

iii.) Poly(N-vinyl formamide). To 2.32 g of the 1:1 molar ratio mixture of N-vinyl formamide (20 mmol) and formamide (20 mmol), 5 mL isopropanol was added. The reaction mixture was purged with argon and freeze-thawed 3 times using liquid nitrogen to eliminate oxygen. 2,2'-Azobisisobutyronitrile (AIBN, 32 mg, 0.12 mmol) was added to the reaction solution, which was then refluxed for 4 h under argon. Isopropanol was removed by rotary vacuum evaporation. The residue was dissolved in a small amount of water and precipitated in acetone. The precipitate was filtered and dried under vacuum at 70° C. overnight to give 1.3 g (89%) of poly(N-vinyl formamide). GPC measurement showed that the number average molecular weight was ~10,000. IR (KBr): 1677 $cm^{-1}$ (amide I), 1538 $cm^{-1}$ (amide II). $^1$H-NMR ($D_2O$, ppm): 1.57 (2H, —$CH_2$—), 3.79 (1H, —CH—), 7.90 (1H, HCO—).

iv) Poly(vinyl amine).hydrochloride (PVAm.HCl). To a 4 mL aqueous solution of 0.85 g (12 mmol) of poly(N-vinyl formamide), 4 mL aqueous NaOH (0.72 g, 18 mmol) solution was added. The mixture was stirred at 80° C. for 6 h under nitrogen. After cooling to ambient temperature, the solution was acidified with concentrated HCl, to precipitate the PVAm.HCl salt. The precipitate was washed with methanol to neutral pH, and dried under vacuum to give 0.62 g (65%) PVAm. HCl. IR (KBr) ~3420 $cm^{-1}$ (v(N—H) of $NH_2$), ~3000 $cm^{-1}$ (wide and strong overlapping peak from v(N—H) of —$NH_3^+$ and v(C—H) of $C_2$ and CH), 1606 and 1512 $cm^{-1}$ (($\delta_{as}$(N—H) and $\delta_s$(N—H) of —$NH_3^+$). No amide peaks were observed. $^1$H-NMR $D_2O$, ppm): 2.16 (2H, —$CH_2$—), 3.74 (1H, —CH—).

Poly(vinyl amine) (PVAm). PVAm was obtained by passing the aqueous solution of PVAm.HCl through a strong anionic exchange column (Amberlite IR-400), followed by lyophilizing the eluate. IR (KBr): ~3300 $cm^{-1}$ (v(N—H) of —$NH_2$), 2870 and 2930 $cm^{-1}$ (v(C—H) of $CH_2$ and CH), 1591 $cm^{-1}$ ($\delta$(N—H) of —$NH_2$). $^1$H-NMR ($D_2O$, ppm): 1.22 (2H, —$CH_2$—), 2.85 (1H, —CH—), $^1$H-NMR (DMSO-$D_6$, ppm): 1.18 (—$CH_2$—), 2.92(—CH—), 2.6 (—$NH_2$) (small amount of PVAm can be dissolved in DMSO-$D_6$ at 60° C.), $^1$H-NMR (DMSO-$D_6$ with a drop of $D_2O$, ppm): 1.20 (2H, —$CH_2$—), 2.88(1H, —CH—).

The PVAm is readily soluble in water and methanol. From the $^1$H-NMR of PVAm in $D_2O$, the peak integration of —$CH_2$—, —CH— agree with the predicted molecular structure. The proton resonance peak of —$NH_2$ was not observed for PVAm in $D_2O$, because of rapid proton exchange between —$NH_2$ and any $H_2O$ in $D_2O$. The proton resonance peak of —$NH_2$ (2.6 ppm) was observed when using vigorously dried DMSO-$D_6$ as solvent. However, after adding a drop of $D_2O$ into the PVAm-DMSO-$D_6$ solution, the peak disappears. The proton peaks of —$CH_2$— and —CH— are broad because of the poor solubility of PVAm in DMSO. In addition, the proton peak of the trace $H_2O$ is shifted, probably due to the interaction between $H_2O$ and DMSO.

C Synthesis of N-Hexanoyloxy Succinimide

To a solution of 4.64 g (0.04 mol) of hexanoic acid and 5.75 g (0.05 mol) of N-hydroxy succinimide in 100 mL distilled DMF, 10.3 g (0.05 mol) of DCCI was added. The mixture was cooled with an ice-water bath and stirred for 5 h. The dicyclohexyl urea (DCU) precipitate was removed by filtration, and the DMF solvent was removed by vacuum rotary evaporation. The yellow oil residue was washed with water and hexane to yield a white solid, which was vacuum dried at 78° C. to give 6.34 g (74%) of N-hexanoyloxy succinimide. IR (KBr): 1816 cm$^{-1}$ (v(C=O) of ester), 1745–1786 cm$^{-1}$ (v(C=O) of imide). $^1$H-NMR (DMSO-d$^6$, ppm): 0.86 (3H, —CH$_3$), 1.31 (4H, —(CH$_2$)$_2$CH$_3$), 1.62 (2H, —CH$_2$CH$_2$COO—), 2.64 (2H, —CH$_2$COO—), 2.80 (4H, —COCH$_2$CH$_2$CO—).

D. Synthesis of Dextran Lactone

Dextran lactone (M$_w$=1600, M$_w$/M$_n$=1.16, DP=9) was prepared as described in Zhang, T.; Marchant, R. E. *Macromolecules* 1994, 27(25), 7302–7308, which is specifically incorporated herein by reference.

E. Synthesis of Surfactant Polymer (PNVDA-co-PNVH) (1:1.06) was prepared by reacting amino groups of PVAm with dextran lactone and N-hexanoyloxy succinimide simultaneously at a molar feed ratio of dextan lactone to N-hexanoyloxy succinimide of 1:1. Specifically, 0.54 g (0.4 mmol) of dextran lactone in 6 mL DMSO was added to a 2 mL methanol solution containing 34.2 mg of PVAm (0.8 mmol amino groups) and 85.2 mg (0.4 mmol) of N-hexanoyl succinimide. After stirring for 4 h at room temperature, the solution was heated to 70° C. with an oil bath and stirred for 2 days. The product solution was concentrated by vacuum distillation and precipitated by the addition of acetone. The precipitate was filtered and dried under vacuum at 78° C. overnight to give 0.53 g (81% yield) raw product. This was purified by extensive dialysis against water as described previously.

EXAMPLE 2

Poly(N-vinyl dextran aldonamide-co-N-vinyl hexanoamide) (PNVDA-co-PNVH) (1:3.7)

(PNVDA-co-PNVH) (1:3.7)was prepared as described above in example 1, except the molar feed ratio of dextran lactone to N-hexanoyloxy succinimide was 1:2.

EXAMPLE 3

Poly(N-vinyl dextran aldonamide-co-N-vinyl hexanoamide) (PNVDA-co-PNVH) (1:5)

(PNVDA-co-PNVH) (1:5)was prepared as described above in example 1, except the molar feed ratio of dextran lactone to N-hexanoyloxy succinimide was 1:4.

EXAMPLE 4

Poly(N-vinyl dextran aldonamide-co-N-vinyl dodecanoamide) (PNVDA-co-PNVL) (1:1.5)

(PNVDA-co-PNVL) (1:1.5) was prepared as described above in example 1 except that PVAm was reacted simultaneously with dextran lactone and N-lauroyloxy succinimide. The molar feed ratio of dextran lactone to N-lauroyloxy succinimide was 1:2.

EXAMPLE 5

Poly(N-vinyl dextran aldonamide-co-N-vinyl dodecanoamide) (PNVDA-co-PNVL) (1:1.06)

(PNVDA-co-PNVL) (1:1.06) was prepared as described above in example 1 except that PVAm was reacted simultaneously with dextran lactone and N-lauroyl succinimide. The molar feed ratio of dextran lactone to N-lauroyl succinimide was 1:1.

Characterization of the Surfactant Polymers of Examples 1–5

A. FITR and $^1$H-NMR Spectroscopies

The surfactant polymers of examples 1–3 were characterized by Fourier transform infrared (FTIR) and $^1$H-NMR spectroscopies and elemental analysis to confirm purity and structure. The results were as follows:

IR: 3310 cm$^{-1}$ (v(O—H)), 2930–2874 cm$^{-1}$ (v(C—H) of CH$_2$ and CH), 1643 cm$^{-1}$ (amide I), 1547 cm$^{-1}$ (amide II), 1149–1032 cm$^{-1}$ (v(C—O)). $^1$H-NMR (DMSO-D$_6$, ppm): 0.85 (—CH$_3$ of hexanoyl groups, CH$_3$(CH$_2$)$_3$CH$_2$CO—), 1.1–1.6 ((CH$_2$)$_3$ of CH$_3$(CH$_2$)$_3$CH$_2$CO— and —CH$_2$13 from PVAm backbone), 2.1 (CH$_2$ of CH$_3$(CH$_2$)$_3$CH$_2$CO—), 3.0–4.1 (—CH— of PVAm backbone and all dextran CH's and CH$_2$'s except the ones at the glycosidic linkages), 4.1–5.3 (all dextran OH's and CH at the glycosidic linkages), 7–8 (—NH— of amide linkages).

The IR results demonstrated qualitatively the expected comb-like structure of PNVDA-co-PNVH. The $^1$H-NMR spectra of the purified surfactants show proton peaks derived from PVAm, dextran and hexanoyl groups, confirming the expected composition for the surfactants.

The compositions for PNVDA-co-PNVHs prepared from the 3 different molar feed ratios were estimated, based on proton integration of $^1$H-NMR spectra. Both theoretical and experimentally determined compositions are Listed in Table 1. The measured compositions are, as expected, lower than the extreme theoretical values calculated by assuming syndiotactic. The polymer surfactants with varied hydrophilic/hydrophobic balances were designated as PNVDA-co-PNVH (1:1), PNVDA-co-PNVH (1:3.7), and PNVDA-co-PNVH (1:5). PNVDA-co-PNVH (1:1) and PNVDA-co-PNVH (1:3.7) are soluble in water, DMF and DMSO, while PNVDA-co-PNVH (1:5) is not readily soluble in water, but is soluble in DMSO. However, PNVDA-co-PNVH (1:5) becomes partially soluble in water with vigorous sonication (1.5 h). An opaque solution can be prepared at low concentration (~1 mg/ml).

B. Surface Active Properties at the Air/Water Interface

Surface active properties of the surfactant polymers of examples 1–3 at an air/water interface were determined from surface tension measurements and compared to the surface active properties, of PNVDA, a homopolymer composed of PVAm with pendant dextran molecules but lacking hydrophobic branches. PNVDA, showed virtually no surface activity, as indicated by the small decrease (~2 dyn/cm) in water surface tension with increasing surfactant concentration. In contrast, the surfactants PNVDA-co-PNVH (1:1) and PNVDA-co-PNVH (1:3.7) exhibit significant surface active behavior, as indicated by a substantial decrease in surface tension with increasing surfactant concentration. The lowest surface tension achieved is about 41 dyn/cm, a decrease of 31 dyn compared with pure water. In both cases, no critical micelle phenomenon was observed within the measured concentration range.

A surfactant's surface activity is characterized by its efficiency and effectiveness. The efficiency is defined by the negative logarithm of the bulk concentration (mol/L) necessary to reduce the surface tension by 20 dyn/cm, designated as pC 20. The pC 20 of PNVDA-co-PNVH (1:1) and PNVDA-co-PNVH (1:3.7) are estimated to be 4.9 and 5.2 respectively, based on an average molecular weight of 50,000 for the polymer surfactants, estimated from the molecular weight of PVAm and the surfactant compositions. Effectiveness is defined by the extent of surface tension reduction attained at the critical micelle concentration, $\pi_{CMC}$. No CMC was observed for either PNVDA-co-PNVH (1:1) or PNVDA-co-PNVH (1:3,7). However, the maximun surface tension reduction of 31 dyn/cm was approximately the same for both surfactants.

The results indicated no significant difference between the surface active properties of PNVDA-co-PNVH (1:1) and PNVDA-co-PNVH (1:3.7). Both surfactants gave similar curves for surface tension versus concentration. Since PNVDA-co-PNVH (1:1) and PNVDA-co-PNVH (1:3.7) exhibit similar effects on water surface tension reduction, it is believed that residual free amine groups do not contribute significantly to the surface active properties, and that packing of hexanoyl groups at the air/water interface, which is responsible for reducing the surface tension, is similar in both cases. The results suggests the surfactants have considerable conformational freedom in order to facilitate comparable hexanoyl packing at the air/water interface.

C. Adsorption and Adhesion to Surfaces of Substrates

The surfactant polymers of examples 1–5 were attached to the hydrophobic surfaces of graphite substrates and polyethylene substrates by immersing the substrates in aqueous solutions containing from about 1 to 2 mg/ml of one of the surfactant polymers.

Figure 3:
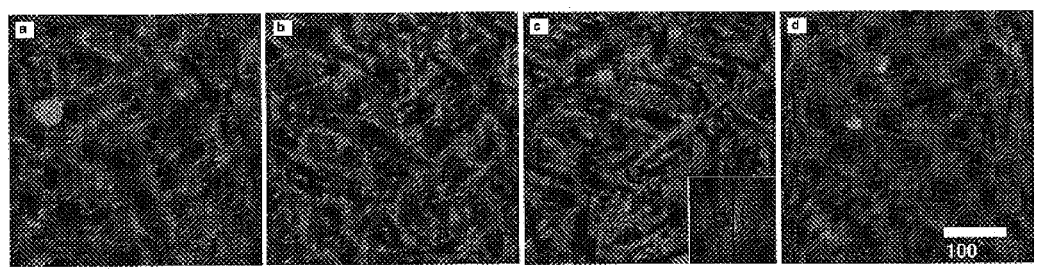
FIG. 3 is a series of AFM images, observed in situ, of adsorbed surfactant polymer, poly(N-vinyl dextran aldonamide-co-N-vinyl hexanamide) with 1:5 dextran to hexanoyl side chain ratio, on the basal plane of graphite. The images (scale bar=250 nm) show the progression of adsorption from: a, ~25 minutes; b, ~1 hour; c, ~5.5 hours; and d,~7.5 hours; as imaged in 0.5 mg/mL polymer solution. (a) Surfactant polymer molecules initially adsorb in strands, driven by hydrophobic interaction and epitaxial adsorption of hexanoyl side chains onto the graphite. (b, c) Additional polymer adsorbs along previously adsorbed chains, as observed by the increasing widths of the adsorbate strips. Epitaxial adsorption is verified by the hexagonal pattern seen in the 2-D fourier transform (inset of c). (d) The graphite surface is almost fully covered by surfactant polymer. Complete monolayer coverage was observed after 20 hours. The height of the adsorbed surfactant polymer is 7–12 Å, indicating a single monolayer.

Real time images of the surfactant polymers adsorbing to highly oriented pyrolytic graphite were obtained using an atomic force microscope (AFM) (Nanoscope III, Digital Instruments) operated in fluid tapping mode. Freshly cleaved graphite was imaged under water prior to the addition of surfactant solution. Imaging of adsorbed surfactant began after the microscope had equilibrated with the new solution (~10 minutes). The results obtained when the graphite substrate was immersed in an aqueous solution containing 0.5 mg/ml of the surfactant polymer of example 3, which has a ratio of 1:5 dextran to hexanoyl groups, are shown in FIG. 3. The initial scans (FIG. 3a) obtained after ~25 minutes, show strands of surfactant polymer adsorbed on the surface. As time progressed, the strands broaden (FIGS. 3b,c) and by ~7 hours (FIG. 3d) most of the surface is covered. Residual surface roughness disappears by 20 hours leaving a complete and compact monolayer. The thickness of the adsorbed surfactant polymer increases slightly with increasing surface coverage up to a maximum of 7–12 Å. This indicates a single monolayer on the surface. Evidence that the adsorption is stable was obtained from observing no discernible change in the monolayer after keeping pure water over the adsorbed surfactant for 1–2 hours and scanning with high AFM imaging forces.

On the graphite, an adsorption pattern of the polymer in strands 60° out of alignment was observed. This pattern was verified by the 2-dimensional Fourier transform of the image showing hexagonal angular dependence. Images of the graphite lattice verified that the strands align perpendicular to the substrate atoms.

Surfactant polymer ordering on graphite propagated laterally, with preferential adsorption at the edge of previously adsorbed polymer. This indicates a self assembling property as well as a surface induced assembly. Epitaxial growth patterns were observed for three surfactant polymers that contained a relatively high concentration of methylene groups relative to glucose residues, i.e., the surfactant polymers of examples 3, 4 and 5. Surfactant polymers with relatively low concentrations of methylene groups to sugar residues, i.e., the surfactant polymers of examples 1 and 6 adsorb to the surface, but not in an ordered pattern. In this case, alkanoyl chains may bind in registry to achieve energy minimization, but are spaced too far apart to induce the polymer backbone to extend. To achieve ordering, enthalpic energy gained from epitaxial adsorption of alkanoyl side chains offsets the entropy loss in extending the polymer backbone and forcing dextran side chains into close proximity.

These results show that alkanoyl side chains assemble on graphite through hydrophobic interaction and epitaxial adsorption. This assembly constrains the polymer backbone to the substrate with solvated dextran side chains protruding into the aqueous phase, creating a glycocalyx-like coating. These results also showed that the time required for attachment of the surfactant polymers to the substrate ranges from a few minutes to several hours. Surfactant polymers having a hydrophobic side chain density from 28–56% of the side groups required only a few minutes to attach.

A monolayer of the surfactant polymer of example 2 was also attached to a low density polyethylene substrate by immersing the substrate in an aqueous solution comprising 1–2 mg/ml of the surfactant polymer for 24 hours. Thereafter the monolayer was air dried, and the stability of the monolayer determined by causing pure water to flow at a rate of 1 ml/min across the modified surface for 4 days and then examining the modified substrate. The desorption of the monolayer from the substrate under these conditions, as determined by water contact measurements and by infrared spectroscopy, was negligible. These results indicate that attachment of the surfactant polymers to the surface of the substrate does not require further surface coupling chemistries.

D. Alteration of the Properties of a Surfactant Polymer Coated Substrate

The hydrophilic nature of the modified surfaces of the surfactant polymer-coated substrates was confirmed by measurement of low water contact angles. Water contact angle measurements were carried out by a sessile-drop method using a Rarne-Hart goniometer at room temperature. Advancing contact angles were measured by placing a 2 $\mu$l water drop on the surface using a microsyringe attachment. Adding second drop to the first one yields another advancing contact angle. Underwater contact angle measurements were done on some of the films by captive bubble (air in water) method. The water contact angles on polyethylene substrates dropped from 92° to 30°–55° when coated with the surfactant polymers of examples 1–5.

A confluent layer of the surfactant polymer of example 3 was attached to a the surface of a graphite substrate by immersion of the substrate in a an aqueous solution containing 2 mg/ml of the surfactant polymer for 24 hours. Thereafter, using a laminar flow cell, a 50% solution of fresh human platelet poor plasma in phosphate buffered saline (pH 7.4) anticoagulated with sodium citrate, was adsorbed on graphite samples, under static conditions for 30 minutes at 37° C. This provided a rigorous in vitro test, since the solution contained all plasma proteins in blood at a concentration that was sufficient to cover a surface with proteins every second of exposure. The protein solution was replaced by PBS and the samples were rinsed under a controlled shear stress of 10 dynes/cm$^2$ for 5 minutes. Samples were air-dried overnight and under partial vacuum.

Figure 4:
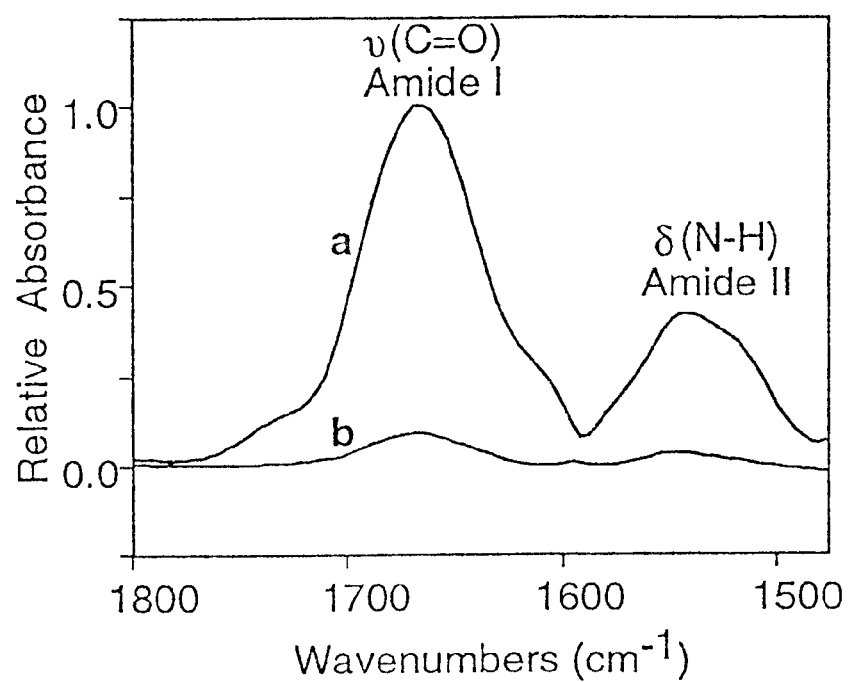
FIG. 4 is the infrared spectra (1800~1400 $cm^{-1}$ region) showing (a) high adsorption of plasma proteins from 50% fresh human platelet poor plasma on graphite, and (b) negligible protein adsorption on graphite surface modified with surfactant polymer (dextran/hexanoyl ratio of 1:5). Protein adsorption was determined from the relative absorbance intensity of the protein Amide I (1650 $cm^{-1}$) and Amide II (1550 $cm^{-1}$) on each surface. IR spectra (ATR mode) were collected by co-adding 100 scans with a resolution of 8 $cm^{-1}$, using an FTS 575C IR spectrometer, equipped with a UMA 500 microscope (Bio-Rad). IR spectra were normalized using the sharp negative peak (1590 $cm^{-1}$) characteristic of the graphite as an internal standard, followed by spectral subtraction of water vapor and the graphite substrate to reveal the protein adsorbate. For 'b', the spectral contribution from amide bonds in the surfactant polymer also was subtracted.

Protein adsorption was quantified from the relative IR (ATR mode) absorbance intensity of the characteristic protein Amide I (1650 cm$^{-1}$) and Amide II (1550 cm$^{-1}$) bands. To reveal the protein adsorbate (FIG. 4), spectra were normalized to a sharp negative peak (1590 cm$^{-1}$) characteristic of the graphite, followed by digital subtraction of water vapor and the graphite substrate. On bare graphite, the Amide I and II bands are attributed entirely to adsorbed proteins, whereas on modified graphite amide bonds in the surfactant polymer and adsorbed proteins contribute to the absorbance. By subtracting the contribution from the surfactant polymer, the absorbance due to adsorbed protein is isolated and determined. As shown in the FIG. 4, Amide I and II protein bands are very strong on bare graphite and almost negligible on the surfactant modified graphite. It is estimated that plasma protein adsorption was suppressed by at least 90% on the polymercoated surface, compared with the bare graphite, which is consistent with a stable adsorbed surfactant polymer. The results also show that the layer is effective in suppressing protein adsorption from human plasma protein solution onto the coated substrate.

Group B

Surfactants comprising a poly(vinyl) backbone linked by secondary amine linkages to a plurality of heparin side chains and a plurality of hydrophobic side chains were prepared by simultaneously reacting PVAm with different molar ratios of alkyl aldehydes and nitrous acid-depolymerized heparin which has an aldehyde end group. Heparin is analogous to the oligosaccharide portion of heparan sulfate, which is abundant on endothelial cell glycocalyx. Formation of the surfactant polymers results from reductive animation between the amines on the polymer and the reactive aldehydes on the alkyl aldehydes and modified heparin molecules.

EXAMPLE 6

Poly(N-vinyl hexyl amine-co-N-vinyl heparin amine) (PNVHA-co-PNVHep A)

A. Materials

Nitrous acid de-polymerized heparin (origin: intestinal mucosa, porcine) with a $M_w$ of 5503 and an aldehyde content of 186 μmol/g was purchased from Pharmacia Hepar, Inc. Acetaldehyde, hexanal (98%), sodium cyanoborohydride (NaBH$_3$CN, 95%) and dimethyl formamide (DMF) were purchased from Aldrich Chemical Co. and used as received. Laurinaldehyde (~97%) was purchased from Fluka Chemik and used as received. Maltonolactone and poly(vinyl amine) (PVAm) were prepared according to the methods reported previously. All other reagents and solvents were used as received unless otherwise specified.

B. Synthesis of Polymer

PVAm was prepared as described above in example 1

C. Synthresis of Dextran Lactone

Dextran lactone ($M_w$=1600, $M_w/M_n$=1.16, DP=9) was prepared as described in Zhang, T.; Marchant, R. E. *Macromolecules* 1994, 27(25), 7302–7308, which is specifically incorporated herein by reference.

D. Synthesis of Surfactant Polymer (PNVHA-co-PNVHepA) was prepared by reacting PVAm with hexanal and nitrous acid depolymerized heparin at a molar feed ration of 1:10 either simultaneously or sequentially. The PVAm was dissolved in methanol and a suitable amount of alkyl aldehyde added to the solution. Thereafter a methanol/water solution containing a suitable amount of heparin and the catalyst NaBH$_3$CN was added to the PVAm-alkyl aldehyde mixture. The reaction was allowed to proceed for 48 hours at room temperature. Thereafter, the reaction was terminated and the surfactant recovered.

EXAMPLE 7

Poly(N-vinyl hexyl amine-co-N-vinyl heparin amine-co-N-vinyl maltonoamide) (PNVHA-co-PNVHep A-co-PNVM)

(PNVHA-co-PNVHep A-co-PNVM) was prepared as described in example 6 except that the PVAm was further reacted with maltonolactone to block any unreacted amine groups on the polymer. The molar feed ratios of hexanal, heparin and maltonolactone were 7:1:2 and 6:2:2.

Group C

Surfactants comprising a poly(vinyl) backbone linked by secondary amine linkages to a plurality of peptide side chains and a plurality of hydrophobic side chains were prepared by simultaneously reacting PVAm with different molar ratios of alkyl aldehydes and with peptides linked to a spacer molecule having a reactive aldehyde at the free end thereof. A suitable spacer molecule is a glutaric dialdehyde molecule that reacts with the free amine end of the peptide and the amine group on the polymer. Another suitable spacer molecules include poly(ethylene oxide) (PEO) dialdehyde spacer or other similar bifunctional molecule. The peptide itself is synthesized to either have a free carboxyl end group or an end that is capped.

Synthesis of the poly(vinyl amine) (PVAm) polymer surfactant requires two steps: (1) modifying the peptide to create a terminal aldehyde group; and (2) simultaneously coupling the modified peptide and an alkyl aldehyde to the polymer backbone using a standard Schiff base reaction with reduction to a secondary amine. In a preferred embodiment, the surfactant polymer comprises two different types of hydrophilic side chains, one being a peptide and the other being an oligosaccharide. For such surfactant polymers, the molar amount of peptide and saccharide can be varied, but the total molar amount of hydrophilic groups should result in a 1:0.5 to 1:2 ratio with hexanal, for solubility reasons.

EXAMPLE 8

Poly(N-vinyl-5-peptidyl-pentylamine-co-N-vinyl hexyl amine (PVAm(Pep:Hex) (1:1.75)

A. Materials

All solvents (synthesis grade N,N-dimethyl formamide (DMF), dichloromethane, 20% piperidine/DMF, and DIPEA), resins, and activator were purchased from Perseptive Biosystems. The FMOC protected amino acids were obtained from AnaSpec. The scavengers (phenol, 1,2 ethanedithiol, triisopropylsilane), sodium cyanoborohydride (NaCNBH$_3$) and hexanal (Aldrich) were used as received. Ultrapure water was delivered from a Millipore-RO system, with hydrocarbon content <5 ppb. Poly(vinyl amine) was prepared as described in example 1. All other reagents were used as received unless otherwise stipulated.

B. Synthesis of the Peptide

The initial peptide was synthesized with a solid phase peptide synthesizer (SPPS), utilizing common solvents, packing resins and capped amino acids. This peptide is an eleven amino acid molecule having the following sequence:

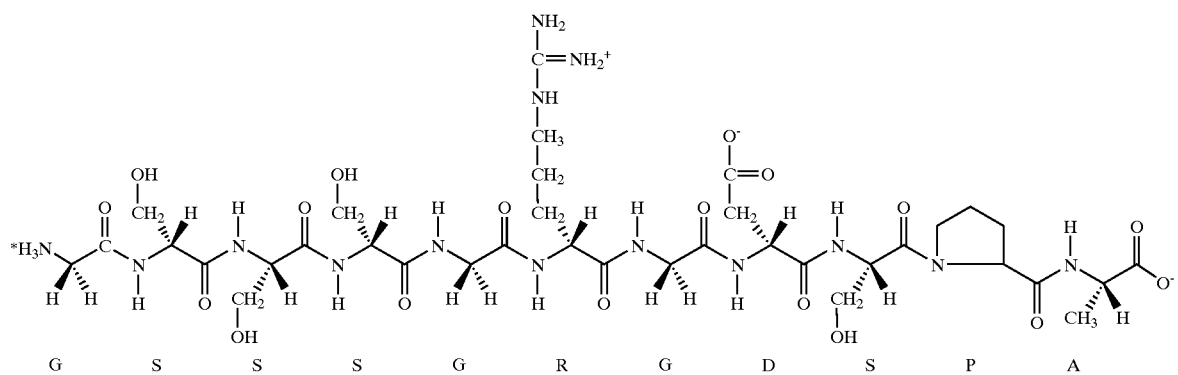

G S S S G R G D S P A

The peptide was then purified by preparatory scale-high performance liquid chromatography (HPLC and characterized for composition by mass spectroscopy and HPLC. An average yield per batch is about 60–80 mg of pure (>98%) product. The product was then stored in a −20° C. freezer to minimize moisture uptake.

C. Peptide Modification

In a small bottom flask, 25.6 mg (0.256 mmol) glutaraldehyde and 3.2 mg (0.0512 mmol) NaCNBH$_3$ was dissolved in 3 mL ultrapure water. A solution of 50 mg (0.0512 mmol) pure peptide in 1 mL ultrapure water was added dropwise. The pH of the solution was adjusted to 6 using HCl, and the flask was sealed and allowed to stir at room temperature for 4 hours. The peptide was purified from excess glutaraldehyde by extensive dialysis against pure water using Spectra Pro 3 regenerated cellulose membrane with 500 molecular weight cutoff.

D. Surfactant Polymer Synthesis

To prepare PVAm(PEP:HEX)(1:1.75), 25.4 mg (0.024 mmol) modified peptide was dissolved in 0.20 mL ultrapure water. (Water must be less than 10% of the final solution volume for the sample to precipitate out in acetone). To this mixture, 3.6 mg (0.036 mmol) hexanal and 3.75 mg (0.06 mmol) NaCNBH$_3$ in 2.0 mL ethanol was added. Finally, 2.565 mg (0.06 mmol) PVAm in 2 mL ethanol was added to the reaction flask dropwise. The pH of the solution was adjusted to 6 using HCl, and the solution stirred for 24 hours at room temperature. The solution was precipitated in 100 mL acetone and dried at room temperature under vacuum overnight. The raw product was further purified by dialyzing against ultrapure water using Spectra Pro 3 regenerated cellulose membranes with 3500 molecular weight cutoff. The purified sample was then lyophilized to obtain the final surfactant product. In general, peptide surfactant polymers with peptide to hexanal ratios between (1:0.5) and (1:2) would be the desirable range.

EXAMPLE 9

Poly(N-vinyl-5-peptidyl-pentylamine-co-N-vinyldextranaldonamine-co-N-vinyl hexyl amine (PVAm (Pep:Dex:Hex))

A surfactant polymer comprising a plurality of hydrophobic side chains, a plurality of oligosaccharide side chains, and a plurality of peptide chains were prepared by reacting the modified peptide and, dextran lactone, and hexanal simultaneously with the PVAm as described above in example 8. The molar ratios of the peptide, dextran lactone, and hexanal were 1:1:3

EXAMPLE 10

Poly(N-vinyl-5-peptidyl-pentylamine-co-N-vinyldextranaldonamine-co-N-vinyl hexyl amine (PVAm (Pep:Dex:Hex))

A surfactant polymer comprising hydrophobic side chains, peptide side chains, and oligosaccharide side chains was prepared by reacting the modified peptide, maltolactone, and hexanal simultaneously with the PVAm as described above in example 8. The molar feed ratios of the peptide, dextran lactone, and hexanal were 3:1:6.

Characterization of the Surfactant Polymers of Examples 8–10

A. FITR and $^1$H-NMR Spectroscopies

The purity of the peptide surfactant polymers after dialysis was verified using IR spectroscopy, which showed that no residual aldehyde peak (at 1740 cm$^{-1}$) was present in the spectrum. The final peptide-to-hexanal ratio was determined using $^1$H-NMR spectroscopy. This was done by taking the integrals of the proton peaks that correspond to each ligand and calculating the final value.

B. Alteration of Surface Properties of Materials Coated with the Surfactant Polymers of Examples 8–10

The surfactant polymers were shown to be surface active on hydrophobic materials, such as octadecyltrichlorosilane (OTS)-derivatized glass. The surfactant was first dissolved in a water/acetonitrile mixture, then the OTS glass was submerged in the solution for 24 hour adsorption. The sample was removed, dried overnight and water contact angle measurements were taken. Typically, the water contact angle dropped from 110 degrees to 20–30 degrees, indicating the successful adsorption of surfactant to the surface. The surfactant-coated OTS was then placed in a low flow chamber where water is constantly flowing over the sample for 24 hours. This procedure tests the adhesion stability of the surfactant on the hydrophobic OTS surface. After drying the sample, contact angle measurements are again taken. Typically the water contact angle increase only about 10 degrees, to about 30–40 degrees, indicating that the surfactant remains firmly attached to the hydrophobic surface.

Figure 5:
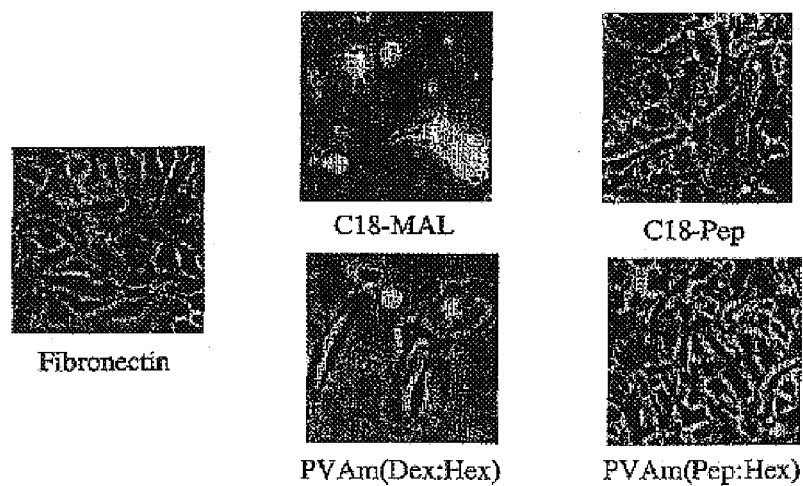
FIG. 5 shows phase contrast images showing the attachment and growth of human umbilical vein endothelial cells on surfactant coated surfaces after 72 hours.

The surfaces with adsorbed peptide surfactant polymers of examples 10 and 11 were shown to promote endothelial cell growth and proliferation. Human umbilical vein endothelial cells (HUVEQ) in HEPES buffer were added to containers having OTS samples coated with the surfactant polymers of examples 8–10. Phase contrast and fluorescent microscopic images were taken after 3, 24 and 72 hours of incubation time. The results at 72 hours for the phase contrast images are shown in FIG. 5. Note that fibronectin coated OTS serves as a positive control for HUVEC growth and proliferation. No cell growth was observed on surfaces coated with the surfactant polymer of example 2 or maltose linear surfactants, as shown by phase contrast microscopy. This result serves as a further demonstration that the surfactant polymers of Group A prevent adhesion of proteins and cells. However, for the peptide surfactant coated surfaces, cell growth was similar to that on fibronectin. Cell growth was also quantified using fluorescent staining for the actin fibers and focal adhesion points to the surface. As shown in FIG. 5, the peptide surfactant polymers grew healthy cells with long actin stress fibers and many focal adhesion points. As the peptide-to-dextran ratio decreased, the cell viability decreased as well. These results indicate that the peptide surfactant polymers have a well-defined structure, stably adsorb to hydrophobic surfaces, and promote cell growth and proliferation.

What is claimed is:

1. A comblike surfactant polymer comprising:
   a) a polymeric backbone of repeating monomeric units;
   b) a plurality of hydrophobic side chains comprising from about 2 to about 18 methylene groups, said plurality of hydrophobic side chains being linked to said polymeric backbone by ester linkages, secondary amine linkages, amide linkages, or combinations thereof; and
   c) a plurality of hydrophilic side chains linked to said polymeric backbone by ester linkages, secondary amine linkages, amide linkages, or combinations thereof, said hydrophilic side chains selected from the group consisting of: neutral oligosaccharide side chains having a weight average molecular weight of less than 7000; charged oligosaccharide side chains having a weight average molecular weight of less than 10,000; an oligopeptide of from about 3 to 30 amino acid residues, said oligopeptide having an amino acid sequence which interacts with protein receptors on the surface of cells; and combinations thereof.

2. The surfactant polymer of claim 1 wherein said polymeric backbone is a derivatized poly(vinyl amine), or a derivatized poly(vinyl alcohol) or a derivatized polylysine.

3. The surfactant polymer of claim 1 wherein said polymeric backbone is linked to said plurality of hydrophobic side chain by amide linkages;
   and wherein said polymeric backbone is linked to a plurality of oligosaccharide side chains by amide linkages.

4. The surfactant polymer of claim 1 wherein said polymeric backbone is linked to said plurality of hydrophobic side chains by secondary amine linkages; and
   wherein said polymeric backbone is linked to a plurality of oligopeptide side chains by secondary amine linkages.

5. The surfactant polymer of claim 1 wherein said polymeric backbone is linked to said plurality of hydrophobic side chains by secondary amine linkages;
   wherein said polymeric backbone is linked to a plurality of oligopeptide side chains by secondary amine linkages;
   and wherein said polymeric backbone is linked to a plurality of oligosaccharide side chains by amide linkages.

6. The surfactant polymer of claim 1 wherein said oligopeptide side chains comprise an amino acid sequence selected from the group consisting of: SEQ ID No. 1 (RGD), SEQ ID No. 4 (RRAR), SEQ ID No. 5 (RRRKRR), SEQ ID No. 6 (PPRRARVT), and SEQ ID No. 7 (PPREVVPRPRP).

7. The surfactant polymer of claim 1 wherein the ratio of hydrophilic side chains to hydrophobic side chains is from about 3:1 to about 1:6.

8. The surfactant polymer of claim 1 wherein said hydrophilic side chains are selected from the group consisting of dextran, oligomaltose, heparin, dermatan sulfate, and dextran sulfate.

9. A substrate having a surfactant polymer attached to a surface thereof, said surfactant polymer comprising:
   a) a polymeric backbone of repeating monomeric units,
   b) a plurality of hydrophobic side chains comprising from about 2 to about 18 methylene groups, said plurality of hydrophobic side chains being linked to said polymeric backbone by ester linkages, secondary amine linkages, amide linkages; or combinations thereof and
   c) a plurality of hydrophilic side chains linked to said polymeric backbone by ester linkages, secondary amine linkages, or amide linkages, or combinations thereof; said hydrophilic side chains selected from the group consisting of: neutral oligosaccharide side chains having a weight average molecular weight of less than 7000; charged oligosaccharide side chains having a weight average molecular weight of less than 10,0000; an oligopeptide of from about 3 to 30 amino acid residues, said oligopeptide having an amino acid sequence which interacts with protein receptors on the surface of cells; and combinations thereof.

10. The substrate of claim 9 wherein said surfactant polymer comprises a plurality of oligopeptide side chains comprising an amino acid sequence selected from the group consisting of: SEQ ID No. 1 (RGD), SEQ ID No. 4 (RRAR), SEQ ID No. 5 (RRRKRR), SEQ ID No. 6 (PPRRARVT), and SEQ ID No. 7 (PPREVVPRPRP).

11. The substrate of claim 9 wherein said surfactant polymer comprises a plurality of oligosaccharide side chains linked to said polymer backbone by amide linkages.

* * * * *

```
                        SEQUENCE LISTING

<160> NUMBER OF SEQ ID NOS:   10

<210> SEQ ID NO 1
<211> LENGTH: 3
<212> TYPE: PRT
<213> ORGANISM: hydrophilic oligopeptide

<400> SEQUENCE: 1

Arg Gly Asp
1

<210> SEQ ID NO 2
<211> LENGTH: 4
<212> TYPE: PRT
<213> ORGANISM: hydrophilic oligopeptide

<400> SEQUENCE: 2

Arg Gly Asp Ser
1

<210> SEQ ID NO 3
<211> LENGTH: 5
<212> TYPE: PRT
<213> ORGANISM: hydrophilic oligopeptide

<400> SEQUENCE: 3

Arg Gly Asp Ser Pro
1               5

<210> SEQ ID NO 4
<211> LENGTH: 4
<212> TYPE: PRT
<213> ORGANISM: hydrophilic oligopeptide

<400> SEQUENCE: 4

Arg Arg Ala Arg
1

<210> SEQ ID NO 5
<211> LENGTH: 6
<212> TYPE: PRT
<213> ORGANISM: hydrophilic oligopeptide

<400> SEQUENCE: 5

Arg Arg Arg Lys Arg Arg
1               5

<210> SEQ ID NO 6
<211> LENGTH: 8
<212> TYPE: PRT
<213> ORGANISM: hydrophilic oligopeptide

<400> SEQUENCE: 6

Pro Pro Arg Arg Ala Arg Val Thr
```

-continued

```
1               5

<210> SEQ ID NO 7
<211> LENGTH: 11
<212> TYPE: PRT
<213> ORGANISM: hydrophilic oligopeptide

<400> SEQUENCE: 7

Pro Pro Arg Glu Val Val Pro Arg Pro Arg Pro
1               5                   10

<210> SEQ ID NO 8
<211> LENGTH: 11
<212> TYPE: PRT
<213> ORGANISM: hydrophilic oligopeptide
<220> FEATURE:
<221> NAME/KEY: misc_feature
<222> LOCATION: (11)..(11)
<223> OTHER INFORMATION: any of the naturally occurring amino acids

<400> SEQUENCE: 8

Gly Ser Ser Ser Gly Arg Gly Asp Ser Pro Xaa
1               5                   10

<210> SEQ ID NO 9
<211> LENGTH: 5
<212> TYPE: PRT
<213> ORGANISM: hydrophilic oligopeptide

<400> SEQUENCE: 9

Arg Arg Lys Arg Arg
1               5

<210> SEQ ID NO 10
<211> LENGTH: 10
<212> TYPE: PRT
<213> ORGANISM: hydrophilic oligopeptide

<400> SEQUENCE: 10

Pro Pro Arg Glu Val Val Pro Arg Pro Arg
1               5                   10
```